US005712413A

United States Patent [19]

Burrington et al.

[11] Patent Number: 5,712,413
[45] Date of Patent: Jan. 27, 1998

[54] PROCESS FOR THE PREPARATION OF N-HYDROCARBYL-SUBSTITUTED AMIDES SUCH AS TERT-BUTYLACRYLAMIDE VIA THE RITTER REACTION USING SOLID HETEROPOLYACID CATALYSTS

[75] Inventors: James D. Burrington, Mayfield Village; Douglas C. Rhubright, Chardon; Chester E. Ramey, Bainbridge Township, Geauga County, all of Ohio

[73] Assignee: The Lubrizol Corporation, Wickliffe, Ohio

[21] Appl. No.: 757,407

[22] Filed: Dec. 4, 1996

[51] Int. Cl.[6] .................................................. C07C 231/06
[52] U.S. Cl. .......................... 564/131; 564/124; 564/126; 564/128; 564/130
[58] Field of Search ............................. 564/125, 126, 564/130, 128, 131

[56] References Cited

U.S. PATENT DOCUMENTS

| | | | |
|---|---|---|---|
| 3,151,157 | 9/1964 | Fugate et al. | 260/561 |
| 4,273,938 | 6/1981 | Merger et al. | 564/124 |
| 5,334,775 | 8/1994 | Gutierrez et al. | 568/780 |
| 5,366,945 | 11/1994 | Kresge et al. | 502/60 |
| 5,387,715 | 2/1995 | Karasawa et al. | 564/124 |

FOREIGN PATENT DOCUMENTS

| | | | |
|---|---|---|---|
| 3-93765 | 9/1989 | Japan | C07C 271/06 |

OTHER PUBLICATIONS

H. Plaut and J.J. Ritter, A New Reaction of Nitriles, VI. Unsaturated Amides *J. Am. Chem. Soc.*, vol. 73 (1951) pp. 4076–4077.

Olah et al., Nafion–H® Catalyzed Beryer–Villiger Oxidation and Ritter Reactions, *Materials Chemistry and Physics*, vol. 17 (1987), pp. 21–30.

*Primary Examiner*—Shailendra Kumar
*Attorney, Agent, or Firm*—David M. Shold; Frederick D. Hunter; Timothy Tesluk

[57] ABSTRACT

Hydrocarbyl-substituted amides are prepared by a process comprising contacting a nitrile with a hydrocarbylating agent, such as an alkylating agent, in the presence of a catalyst comprising a heteropolyacid or salt thereof.

68 Claims, No Drawings

PROCESS FOR THE PREPARATION OF N-HYDROCARBYL-SUBSTITUTED AMIDES SUCH AS TERT-BUTYLACRYLAMIDE VIA THE RITTER REACTION USING SOLID HETEROPOLYACID CATALYSTS

BACKGROUND OF THE INVENTION

The present invention relates to an improved process for the preparation of N-hydrocarbyl-substituted amides.

It is known to react secondary and tertiary alcohols, olefins and water, or esters with nitriles in the presence of acids, such as sulfuric acid, to give N-alkyl-substituted amides. This reaction is known as the Ritter reaction. H. Plaut and J. J. Ritter, A New Reaction of Nitriles. VI. Unsaturated Amides, J. Am. Chem. Soc., vol. 73 (1951), pp. 4076–4077, discloses the reaction of nitriles with olefins or alcohols to yield N-substituted amides, in particular, unsaturated amides.

U.S. Pat. No. 3,151,157, Fugate et al., Sep. 29, 1964, discloses the preparation of N-alkylacrylamide by reacting a straight chain olefin and acrylonitrile in the presence of strong sulfuric acid in a preformed reaction product of said olefin, acrylonitrile and strong sulfuric acid.

It is known to promote Ritter reactions with organic cation exchangers, such as Nafion-H®, a perfluorinated sulfonic acid resin. U.S. Pat. No. 4,273,938, Merger et al., Jun. 16, 1981 discloses the preparation of N-substituted carboxylic acid amides by reacting cyano compounds, e.g., acrylonitrile, with olefins and water in the presence of organic cation exchangers containing sulfonic acid groups. Olah et al., Nafion-H® Catalyzed Baeyer-Villiger Oxidation and Ritter Reactions, Materials Chemistry and Physics, vol. 17 (1987), pp. 21–30, discloses the use of Nafion-H® to promote the reaction of alcohols in the presence of nitriles to yield amido compounds.

Japanese Patent 3-93765, Izumi, filed Sep. 4, 1989, issued Apr. 18, 1991, discloses the use of a molybdic or vanadic heteropolyacid or a salt thereof as in conjunction with palladium chloride in the presence of carbon dioxide to catalyze the formation of aromatic urethane from an aromatic nitro compound with an hydroxy-containing compound.

U.S. Pat. No. 5,334,775, Gutierrez et al., Aug. 2, 1994, discloses the use of heteropolyacids to alkylate hydroxyaromatic compounds with polymer alkylating agents of at least 500 number average molecular weight, and having at least one carbon-carbon double bond. Phosphotungstic acid is claimed as a catalyst for the process.

U.S. Pat. No. 5,366,945, Kresge et al., issued Nov. 22, 1994, discloses the use of a heteropolyacid catalyst supported on a mesoporous crystalline material to catalyze the isomerization of paraffins and the alkylation of aromatic species. The supported heteropolyacids claimed comprise at least one element selected from the group consisting of P, Si, B, Ge, As, Se, Ti, Zr, Mn, F, V, Ce, and Th as a central element, and Mo and/or W as a coordinating element.

The use of heteropolyacids or salts thereof as co-catalysts in the preparation of alpha-hydroxy-isobutyramide is known. U.S. Pat. No. 5,387,715, Karasawa et al., Feb. 7, 1995, discloses the preparation of α-hydroxy-isobutyramide by hydrating acetone cyanohydrin in the presence of manganese dioxide in the further presence of a particular oxide dissolved in water, oxoacid, heteropolyacid or a salt of the acids.

SUMMARY OF THE INVENTION

The present invention provides a process for the preparation of an N-hydrocarbyl-substituted amide, comprising contacting:

(a) a nitrile with (b) a hydrocarbylating agent, in the presence of (c) a catalyst comprising a heteropolyacid or salt thereof under conditions leading to the formation of the N-hydrocarbyl-substituted amide. The invention further provides the product prepared thereby.

DETAILED DESCRIPTION OF THE INVENTION

The present invention provides a process for the preparation of an N-hydrocarbyl-substituted amide, comprising contacting a nitrile with a hydrocarbylating agent in the presence of a catalyst comprising a heteropolyacid or salt thereof under conditions leading to the formation of the hydrocarbyl-substituted amide. The invention further provides the product prepared thereby.

The process according to the invention in the case where an alcohol is employed as the hydrocarbylating agent is represented graphically as shown:

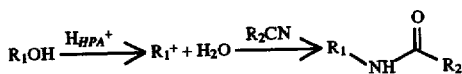

wherein $R_1$ and $R_2$ denote hydrocarbyl, $R_1^+$ denotes a carbonium ion, and $H_{HPA}^+$ denotes a heteropolyacid or salt thereof. The process according to the invention in the case where an olefin is employed as the hydrocarbylating agent is represented graphically as shown:

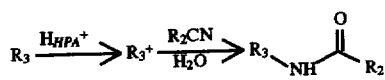

wherein $R_3$ denotes an olefin and $R_3^+$ denotes the carbonium ion formed by the operation of a heteropolyacid or salt upon an olefin. In the case where an olefin is employed as the hydrocarbylating agent, contacting at least one mole of water per mole of olefin $R_3$ with the nitrile $R_2$ in the presence of the heteropolyacid or salt $H_{HPA}^+$ is conducive to the formation of the N-hydrocarbyl-substituted amide product.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

REAGENT ONE: NITRILE

Nitriles are a diverse category of compounds which are characterized by a cyano group, —CN, directly attached to the remainder of the molecule. As illustrated below, a wide variety of nitriles can be used in the Ritter reaction. The nitriles of the present invention have the formula $R_2CN$, where $R_2$ denotes hydrogen, a hydrocarbyl, or a second cyano group. The hydrocarbyl $R_2$ groups of the nitriles will usually comprise hydrocarbon substituents, but can also comprise substituted hydrocarbon substituents and hetero substituents.

The hydrocarbon substituent $R_2$ groups will usually include aliphatic, e.g., alkyl or alkenyl groups, but can also include aromatic groups; and aliphatic- or aromatic-substituted aromatic groups.

The substituted hydrocarbon substituent $R_2$ groups of the nitriles of the present invention will usually include aliphatic, aromatic, and aliphatic- or aromatic-substituted aromatic groups which can be substituted with such non-hydrocarbon groups as halo—for example chloro and fluoro; hydroxy; alkoxy; nitro; amino; and alkyl-substituted amino.

The hetero substituent $R_2$ groups of the nitriles contain such heteroatoms as nitrogen and oxygen.

For purposes of the present invention, the preferred nitriles are aliphatic nitriles. The nitriles can be saturated, or preferably, unsaturated. In one embodiment, the $R_2$ group of the nitrile is an alkenyl group, more preferably a vinyl group. In another embodiment, the $R_2$ group of the nitrile is an alkyl group, preferably a propyl group.

Typical Nitriles

A typical aliphatic nitrile moiety useful in the present invention having an alkenyl hydrocarbon substituent $R_2$ group is acrylonitrile. A typical aliphatic nitrile moiety useful in the present invention and having an alkyl hydrocarbon substituent $R_2$ group is butyronitrile. For such reasons as cost, availability, performance, and similar considerations, the $R_2$ group of the nitrile of the present invention is normally an alkenyl nucleus or an alkyl nucleus. Most preferably the $R_2$ group is a vinyl group. Thus, the most preferred nitrile of the present invention is acrylonitrile. In another embodiment, the nitrile can be a saturated nitrile, such as butyronitrile.

Illustrative Nitriles

A wide variety of other materials can serve a function similar to the typical nitriles of the present invention. Such materials include aliphatic nitriles having alkyl or alkenyl hydrocarbon substituent $R_2$ groups, cyclic nitriles having aromatic, aromatic-, aliphatic-, or non-hydrocarbon-substituted $R_2$ groups, aliphatic nitriles having substituted hydrocarbon substituent $R_2$ groups, nitriles having hetero substituted substituent $R_2$ groups, and dinitriles.

Illustrative aliphatic nitrile moieties useful in the present invention and having alkyl hydrocarbon substituent $R_2$ groups are represented graphically as shown:

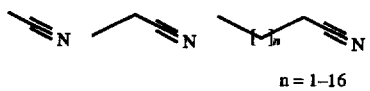

n = 1–16

Illustrative aliphatic nitrile moieties having alkenyl hydrocarbon substituent $R_2$ groups are represented graphically as shown:

Illustrative cyclic nitrile moieties of the present invention having aromatic, aromatic-, aliphatic-, or non-hydrocarbon-substituted $R_2$ groups are represented graphically as shown:

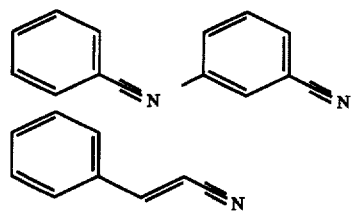

Illustrative dinitrile moieties are represented graphically as shown:

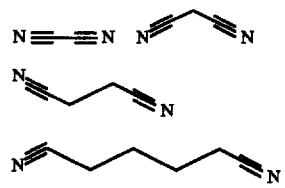

Among these dinitrile moieties, adiponitrile is preferred.

REAGENT TWO: HYDROCARBYLATING AGENT

The nitrile is reacted with a hydrocarbylating agent under under conditions leading to the formation of the hydrocarbyl-substituted amide. The term "hydrocarbylating agent" is analogous to the conventional term "alkylating agent" except that it further encompasses hydrocarbyl groups as distinguished from solely alkyl or substituted alkyl groups. Hydrocarbyl groups are materials which may have a relatively small number of heteroatoms or substituents which do not impede the reaction and do not alter the substantially aliphatic hydrocarbon nature of the group, consistent with the commonly understood meaning of the term "hydrocarbyl."

A hydrocarbyl group evinces a substantially aliphatic hydrocarbon nature for the purposes of the present invention if it is susceptible to formation into a carbonium ion, represented graphically as shown:

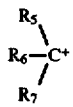

wherein $R_5$, $R_6$, and $R_7$ are independently hydrogen or hydrocarbyl. Preferably, at least one of $R_5$, $R_6$, and $R_7$ is hydrocarbyl.

The preferred hydrocarbylating agents of the present invention are in fact alkylating agents. Alkylating agents are materials which react with another material, under appropriate conditions, typically acid catalyzed conditions, to add an (or an additional) alkyl group on the other material. Alkylating agents are well known materials and include alcohols and the reactive equivalents of alcohols. More specifically, alkylating agents include alcohols, olefins, esters, hydroxy esters, carboxylic acids, ketones, ethers, and alkyl halides.

For purposes of the present invention, the preferred hydrocarbylating agents are alcohols, more preferably mono-alcohols. The alcohols can be primary, or preferably secondary, or more preferably tertiary. In one embodiment, the alcohol contains 4 to 22 carbon atoms, preferably 4 to 16, and more preferably 4 to 10 carbon atoms. Olefins are also useful as hydrocarbylating agents for purposes of the present invention. The olefins can be straight chain or, preferably, branched. In one embodiment the olefin contains 2 to 24 carbon atoms, preferably 3 to 16, and more preferably 4 to 8 carbon atoms.

Typical Hydrocarbylating Agents

A typical tertiary mono-alcohol moiety useful as a hydrocarbylating agent in the present invention is tert-butyl alcohol. Other typical tertiary mono-alcohol moieties include 2,4,4-trimethyl-2-pentanol and 4-oxo-2-methylpentanol. A typical secondary mono-alcohol moiety is 2-propanol. A primary alcohol is 2,4,4-trimethyl-1-pentanol, which may rearrange during reaction to provide a tertiary cation. A typical anhydride moiety is 2-methyl-2-propenyl succinic anhydride. Typical α-olefin moieties include 2-methyl-1-propene, 2,4,4-trimethyl-1-pentene, and 1-propene. A typical β-olefin moiety useful as a hydrocarbylating agent in the present invention is 2,4,4-trimethyl-2-pentene. A typical halo-substituted olefin moiety is 1-chloro-isoprene. A typical di-olefin moiety is 1,3-butadiene. A typical non-hydrocarbon-substituted olefin moiety 1-carboxy-2-methyl propene. A typical ether moiety is the cyclic ether oxirane. A typical ketone moiety is acetone. An example of an alcohol hydrocarbylating agent is EMKROX® AF-20, a propoxylated alcohol, which has alkoxy structure in addition to alcohol functionality, and is represented graphically as shown:

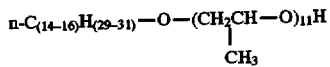

Related materials include other alkoxylated alcohols, including mixtures of alkoxy-related alcohols such as ethoxylated, propoxylated, and butoxylated alcohols.

For such reasons as cost, availability, performance, and similar considerations, the hydrocarbylating agent of the present invention is normally an alcohol or a reactive equivalent thereof, such as an acetal. Preferably, the alcohol is a mono-alcohol. Most preferably the hydrocarbylating agent is a tertiary mono-alcohol. Thus, the most preferred hydrocarbylating agent of the present invention is tert-butyl alcohol.

In another embodiment, the hydrocarbylating agent can be a tertiary mono-alcohol such as 2,4,4-trimethyl-2-pentanol or 4-oxo-2-methylpentanol.

In yet another embodiment, the hydrocarbylating agent can be a secondary mono-alcohol such as 2-propanol.

In a further embodiment, the hydrocarbylating agent can be an anhydride such as 2-methyl-2-propenyl succinic anhydride.

In another embodiment, the hydrocarbylating agent can be an α-olefin such as 2-methyl-1-propene, 2,4,4-trimethyl-1-pentene, or 1-propene.

In yet another embodiment, the hydrocarbylating agent can be a such as 2,4,4-trimethyl-2-pentene.

In a further embodiment, the hydrocarbylating agent can be a halo-substituted olefin such as 1-chloro-isoprene.

In another embodiment, the hydrocarbylating agent can be a di-olefin such as 1,3-Butadiene.

In yet another embodiment, the hydrocarbylating agent can be a non-hydrocarbon-substituted olefin such as 1-carboxy-2-methyl propene.

In a further embodiment, the hydrocarbylating agent can be a ketone such as acetone, $CH_3C(O)CH_3$ or its acetal form, such as $CH_3C(OCH_3)_2CH_3$.

In another embodiment, the hydrocarbylating agent can be a non-hydrocarbon substituted moiety such as a propoxylated alcohol.

Illustrative Hydrocarbylating Agent Alcohols

A wide variety of materials can serve a function similar to the typical hydrocarbylating agent alcohols of the present invention. Such materials include various primary alcohols; aliphatic, alicyclic, and alicyclic-substituted secondary alcohols; aromatic-, aromatic- and alicyclic-, or halo- (e.g., chloro- or bromo-) substituted secondary alcohols; alkyl- and aromatic-substituted aliphatic tertiary alcohols; tertiary alcohols having both aromatic and alicyclic substituents, or cyclic substituents wherein the ring is completed through another portion of the molecule (e.g., two substituents together form an alicyclic radical); tertiary alcohols having an olefinic bond; amido-, amino-, nitro-, carboxy-, halo- (e.g., fluoro- and/or chloro-), alkoxy-substituted tertiary alcohols; and hetero-substituted tertiary alcohols.

Illustrative primary alcohols useful as hydrocarbylating agent moieties in the present invention include ethanol, propanol, linear and branched 1-alkanols having 4 to 24 carbon atoms, cyclohexylmethanol, benzyl alcohol, and substituted benzyl alcohols (methyl, dimethyl, methoxy, etc.)

Illustrative aliphatic, alicyclic, and alicyclic-substituted secondary alcohols include 2-propanol, 2-butanol, 2-pentanol, 3-pentanol, 2-hexanol, 2-heptanol, 2-ethylhexanol, cyclopentanol, cyclohexanol, and 1-cyclohexylethanol.

Illustrative aromatic-, aromatic- and alicyclic-, or halo- (e.g., chloro- or bromo-) substituted secondary alcohols useful as hydrocarbylating agent moieties in the present invention include α-methylbenzyl alcohol, α-ethylbenzyl alcohol, α-chloroethylbenzyl alcohol, α-sec-propylbenzyl alcohol, α-cyclohexylbenzyl alcohol, cumyl alcohol (2-phenylisopropanol), dicumylalcohol, and benzhydrol.

Illustrative alkyl- and aromatic-substituted aliphatic tertiary alcohols include tert-butanol, tert-pentanol, 3-methyl-3-hexanol, and α,α-dimethylbenzyl alcohol.

Illustrative tertiary alcohols having both aromatic and alicyclic substituents, or cyclic substituents wherein the ring is completed through another portion of the molecule (e.g., two substituents together form an alicyclic radical) useful as hydrocarbylating agent moieties in the present invention include 1-methylcyclohexanol, 1-phenylcyclohexanol, and 1-adamantanol.

Illustrative tertiary alcohols having an olefinic bond and useful as hydrocarbylating agent moieties in the present invention include 3-methylhex-1-ene-3-ol and 3-methyl-1-phenylhept-1-ene-3-ol.

The hydrocarbylating agent moieties can also include amido-, amino-, nitro-, carboxy-, halo- (e.g., fluoro- and/or chloro-), and alkoxy-substituted tertiary alcohols, and hereto-substituted tertiary alcohols.

Glycols can also function as hydrocarbylating agents in the present invention.

Illustrative Hydrocarbylating Agent Olefins

A wide variety of materials can serve a function similar to the typical hydrocarbylating agent olefins of the present invention. Such materials include various aliphatic and alicyclic-substituted α-olefins; aryl-substituted α-olefins; aliphatic β-olefins; aryl-substituted β-olefins; hereto-substituted β-olefins; cyclic olefins; and di-olefins.

Illustrative aliphatic and alicyclic-substituted α-olefins useful as hydro-carbylating agent moieties in the present invention include ethylene, propylene, butylene, and other linear and branched α-olefins including 2-methylpropene, 2-methyl-1-butene, and 2-methyl-3-chloropropene.

Illustrative aryl-substituted α-olefins useful as hydrocarbylating agent moieties include styrene and the various ring- and α-substituted styrenes, and homologues such as 3-phenyl-1-propene.

Illustrative aliphatic β-olefins include 2-butene, 3-methyl-2-butene, and 2-methyl-2-pentene.

Illustrative aryl-substituted β-olefins useful as hydrocarbylating agent moieties in the present invention include phenylpropene and substituted versions thereof.

Illustrative cyclic olefins useful as hydrocarbylating agent moieties include cyclohexene and substituted cyclohexenes.

Illustrative di-olefins include 1,4-butadiene, 2,5-hexadiene, divinylbenzene, di(1-ethylvinyl)benzene, dicyclopentadiene, and tricyclohepta-2,5-diene.

Other Illustrative Hydrocarbylating Agents

A wide variety of materials can serve a function similar to the typical hydrocarbylating agent olefins, alcohols, anhydrides, ketones, and ethers of the present invention. Such materials include various esters; carboxylic acids; glycols; ethers; alkyl halides; aldehydes; and ketones.

Illustrative carboxylic acids useful as hydrocarbylating agent moieties in the present invention include acetic acid, propionic acid, butyric acid, other alkanoic acids, trimethylacetic acid, stearic acid, and oleic acid.

Illustrative esters useful as hydrocarbylating agent moieties include the esters of each of the foregoing carboxylic acids, including methyl acetate, ethyl acetate, and other alkyl alkanoates.

Illustrative glycols include ethylene glycol, 1,2-propylene glycol, and glycerol.

Illustrative ethers useful as hydrocarbylating agent moieties in the present invention include diethyl ether, methyl propyl ether, dipropyl ether, and methyl butyl ether, as well as diethers and polyethers.

Illustrative alkyl halides useful as hydrocarbylating agent moieties include preferably, tert-butyl chloride.

Aldehydes and ketones can also function as hydrocarbylating agents for purposes of the present invention. Illustrative aldehydes include formaldehyde, acetaldehyde, propionaldehyde, pentanaldehyde, benzaldehyde, and cyclohexanaldehyde. Illustrative ketones useful as hydrocarbylating agents include acetone, butanone, cyclohexanone, methyl ethyl ketone, acetophenone, and substituted versions thereof.

For such reasons as cost, availability, performance, and similar considerations, the hydrocarbylating agent of the present invention is normally a mono-alcohol. Most preferably the hydrocarbylating agent is a tertiary mono-alcohol. Thus, the most preferred hydrocarbylating agent of the present invention is tert-butyl alcohol.

CATALYST: HETEROPOLYACID

Reactions of a nitrile and a hydrocarbylating agent to form an N-hydrocarbyl-substituted amide are generally acid-promoted reactions. The term "acid-promoted" instead of "acid-catalyzed" is used to describe the action of an acid in the context of a conventional Ritter reaction because the acid employed therein, usually sulfuric acid, is consumed in the reaction or during the subsequent workup, generating at least one mole of sulfate waste per mole of product.

In contrast to sulfuric acid, the ideal catalyst remains substantially unaltered by the reaction in which it participates. The heteropolyacids employed for the amide synthesis reactions of the present invention retain catalytic activity over the course of several Ritter reactions, thus evincing the sustained catalytic activity properties of the ideal catalyst. These properties are markedly absent in the acids used to promote conventional Ritter reactions. Thus the term "acid-promoted" rather than "acid-catalyzed" is used to describe the action of non-heteropolyacids in the reaction of a nitrile and a hydrocarbylating agent to form an N-hydrocarbyl-substituted amide.

In addition, sulfuric acid-promoted Ritter reactions generate at least one mole of sulfate waste per mole of product. The sulfate waste must then be disposed of in accordance with applicable environmental regulations, often at considerable cost. In contrast, the solid acids employed for the amide synthesis reactions of the present invention are heteropolyacids which evince catalytic activity over the course of several Ritter reactions and which do not generate sulfate waste. Moreover, the product can be separated from the solid reactants and the catalyst without quenching, neutralization, or water washing. Thus, the system is amenable to operation under continuous stirred tank reaction or plug flow reaction conditions, in which the catalyst solids are retained in the reactor and liquid products are removed.

Heteropolyacids have the following advantages compared to other catalysts: the absence of by-products produced in reactions of the conjugate base of the acid; thermal and oxidative stability; and the possibility of adjusting catalytic properties by varying the counterion or by varying the heteroatoms or metal atoms; and the possibility of recycling and regenerating the catalyst.

Heteropolyacid catalysts are known materials for the alkylation of aromatic and hydroxyaromatic compounds. These catalysts can exist as the free acid or a salt of the heteropolyanion. Heteropolyanions are polymeric oxoanions formed by a condensation reaction of two or more different oxoanions, e.g.,

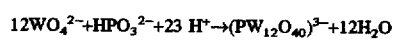

A variety of structures are known for these materials; they can have, for instance, the so-called Keggin structure, wherein twelve $WO_6$ octahetra surround a central $PO_4$ tetrahedron (in the case where phosphorus is employed). Other structures and related formulas are also known, including $PW_{12}O_{42}$, $PW_{18}O_{62}$, $P_2W_5O_{23}$, $PW_9O_{32}$, and $PW_6O_{24}$, where P and W are taken as representative elements. The central atom of the Keggin structure, which is typically phosphorus, as shown, can also be any of the Group IIIA to Group VIIA metalloids or non-transition metals, including P, As, Si, Ge, B, Al, Sb, and Te. The tungsten (W) in the above formula fills the role known as the "poly atom," which can be any of the Group VB or VIB transition metals, including W, V, Cr, Nb, Mo, or Ta. Thus suitable materials include preferably phosphomolybdates, phosphotungstates, silicomolybdates, and silicotungstates. Other combinations selected from among the above elements are also possible, including borotungstates, titanotungstates, stannotungstates, arsenomolybdates, teluromolybdates, aluminomolybdates, and phosphovanadyltungstates, the latter representing a mixed material having a formula (for the anion portion) of $PW_{11}VO_{40}$. The preferred material is a phosphotungstate, which term generally encompasses both the acid and the various salts, described below.

The heteropoly catalysts are active both as their acid form, in which the anion is associated with the corresponding number of hydrogen ions, in the fully salt form, in which the hydrogen ions have been replaced by other cations such as metal ions, or in the partially exchanged salt form, in which a portion of the hydrogen ions have been thus replaced. The exact stoichiometry of these material will depend on the identity of the metals and metalloids employed in their structure. Thus a common and useful material in the acid form is $H_3PW_{12}O_{40}$. The corresponding material in the cesium salt form is $Cs_3PW_{12}O_{40}$; various partially exchanged forms, including specifically $Cs_{2.5}H_{0.5}PW_{12}O_{40}$, are also particularly useful in the present invention. In the latter material, 2.5 of the three original hydrogen ions are replaced by cesium ions. This is a relatively well defined chemical; the fractional coefficients of the Cs and the H indicate that an alternative empirical formula would be $Cs_5HP_2W_{24}O_{80}$, but the former expression is more commonly employed.

For more detailed information on the structures of heteropoly catalysts, attention is directed to Misono, "Heterogeneous Catalysis by Heteropoly Compounds of Molybdenum and Tungsten," Catal. Rev.-Sci. Eng., 29(2&3), 269–321 (1987), in particular, pages 270–27 and 278–280.

Heteropoly acids and salts are commercially available materials, (e.g., Aldrich Chemical Company, #22,420-0) which are generally prepared by dissolving the strongly acidic molybdenum or tungsten oxides $MoO_3$ and $WO_3$ in aqueous NaOH to form the discrete tetrahedral molybdate $MoO_4^{2-}$ and tungstate $WO_4^{2-}$ ions, as shown here:

$$MoO_3 + 2NaOH = 2Na^+ + MoO_4^{2-} + H_2O$$

$$WO_3 + 2NaOH \rightarrow 2Na^+ + WO_4^{2-} + H_2O$$

Heteropolyanions can then be formed by acidifying a molybdate or tungstate solution in the presence of phosphate, silicate or metal ions. The second anion provides a center around which the $MoO_6$ or $WO_6$ octahedra condense, by sharing oxygen atoms with other octahedra and with the central group. The central groups are often oxoanions such as $PO_4^{3-}$, $SiO_4^{4-}$ compounds, and $BO_4^{3-}$, but other elements including Al, Ge, Sn, As, Sb, Se, Te, I and many of the transition elements will serve as the second group. The ratio of $MoO_6$ to $WO_6$ octahedra to P, Si, B or other central atom is usually 12:1, 9:1 or 6:1, although other ratios occur less commonly.

The formation of polyacids is a prominent feature of the chemistry of Mo and W. Other transition elements such as V, Nb, Ta and U also form polyacids, but to a lesser extent. The polyanions contain $MoO_6$ or $WO_6$ octahedra, which are joined together in a variety of ways by sharing corners or edges. The polyacids of Mo and W are divided into isopolyacids and the heteropolyacids of the present invention. In isopolyacids, the anions which condense together are all of the same type, for example all $MoO_6$ groups or all $WO_6$ groups. In heteropolyacids, two or more different types of anion condense together, for example molybdate or tungstate groups with phosphate, silicate or borate groups. The first step in polyacid formation as the pH is lowered must be to increase the coordination number of Mo or W from 4 to 6 by adding water molecules. The relationship between the stable species so far known is:

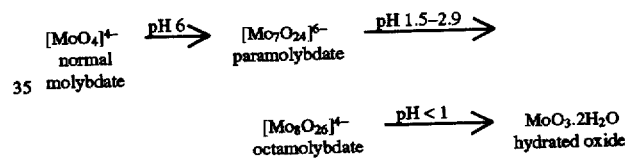

The present understanding of the tungstates may be summarized as follows:

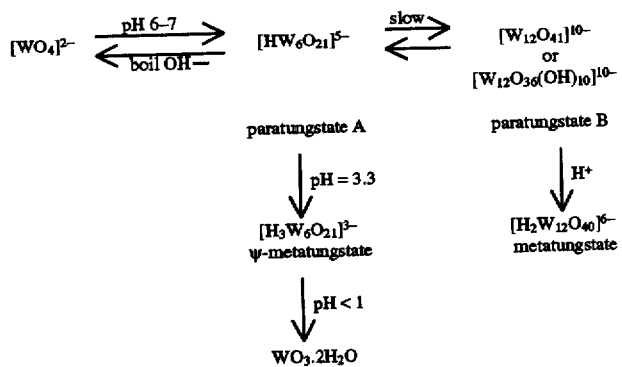

The heteropolyacid salts are similarly commercially available. Alternatively, they can be prepared from the acid materials by neutralization with an appropriate amount of metallic base. For instance, the above-mentioned $Cs_{2.5}$ salt is prepared by neutralization of $H_3PW_{12}O_{40}$ with 2.5 equivalents of cesium hydroxide. The product is isolated by evaporation of the excess water.

Heteropoly acids are generally received in a hydrated form. They can be successfully employed in this form (uncalcined) or they can be treated (calcined) to remove some or all of the water of hydration, that is, to provide a dehydrated species, which sometimes exhibits improved reactivity. Calcining can be conducted by simply heating the hydrated material to a suitable temperature to drive off the desired amount of water. The heating can be under ambient pressure or reduced pressure, or it can be under a flow of air or an inert gas such as nitrogen. The calcining is preferably conducted at a temperature of at least 150° C., preferably at least 200° C., more preferably at least 250° C., for instance, at 320° C. The length of time required for the calcining is typically at least 30 minutes; preferably at least 1 hour, more preferably at least 2 hours or even 3 hours. The upper limits of temperature and time are defined largely by the economics of the process; temperatures much over 350° C. do not generally provide much advantage, nor do times in excess of about 5 hours.

The catalyst can be employed as particles of the pure acid or salt, or it can be provided on a solid support of an inert material such as alumina, silica/alumina, an aluminophosphate, a zeolite, carbon, clay, or, preferably, silica. The catalyst can be coated onto the support by well-known catalyst impregnation techniques, e.g., by applying the catalyst as a solution following by drying. If a support such as silica is employed, the ratio of the active catalyst component to the silica support will preferably be in the range of 0.5:99.5 to 50:50 by weight, preferably 3:97 to 40:60 by weight, and more preferably 10:90 to 30:70 by weight.

The actual process of hydrocarbylation of the nitriles can be either a continuous or batchwise process in which the nitrile, the hydrocarbylating agent and the catalyst are contacted for a suitable period of time, often at an elevated temperature. The components can be reacted neat, typically with excess nitrile. However, an inert solvent such as hexane or cyclohexane can be employed.

The reaction can be conducted under conditions such that the nitrile and the hydrocarbylating agent are present in the gas phase; however, more commonly a liquid phase reaction is more convenient and is thus preferred. Thus the mixture of reagents and catalyst can be contacted generally from room temperature or above, up to a temperature determined largely by the onset of decomposition of the materials or, if a liquid phase reaction is desired, the boiling point of the lowest boiling component of the mixture. Typically, for a liquid phase reaction, the temperature will be 50° to 250° C., preferably 100° to 200° C., more preferably 135° or 145° to 160° C. Higher temperatures, e.g., 250° to 450° C., can be employed for a gas phase reaction if necessary. Elevated pressures can be used if desired, but for ease of operation, operation at ambient pressure is employed or, alternatively, at a pressure modestly in excess of ambient, e.g., sufficient to cause the reactants and products to pass through a reactor in a continuous process.

If the reaction is conducted in a batchwise manner, it can be run in a stirred reactor vessel into which the materials are charged. If the reaction is conducted continuously, it can be run in a continuous stirred tank reactor or, preferably, in a continuous plug flow process, e.g., in a tubular reactor. In a stirred reactor, the catalyst will normally reside within the reactor vessel. At the conclusion of a batchwise process, the catalyst will be removed from the products be suitable means, such as decantation, filtration, or centrifugation. In a continuous tank process, the catalyst will be retained in the reactor by other means which will be apparent to those skilled in the art of reactor design. In a continuous tubular reactor, the catalyst will normally be present as a fixed bed.

The amount of the catalyst employed will typically be 0.1 to 50 percent by weight, based on the weight of the nitrile reacted, and preferably 1 to 15 percent. These amounts are particularly directed to the reaction when it is conducted batchwise. When the reaction is run continuously, the mount of catalyst is better expressed in terms of liquid hourly space velocity, which is the mass of product obtained from the reactor per hour, per unit mass of catalyst employed. Continuous reactions as contemplated by the present invention typically exhibit a liquid hourly space velocity of 0.01 to 100, preferably 1 to 10, depending on temperature and other variables.

In the present process the catalyst can be replaced after every batch, but it is more economical to recycle the catalyst for multiple batches, or to run a continuous process for a relatively long period of time using the same catalyst. After extended use, however, the activity of the catalyst may diminish. An advantage of the present catalyst system is that the catalyst can be reactivated, or regenerated. Possible regeneration procedures known to those skilled in the art including solvent washing, heat treatment, or steaming followed by heat treatment. See M. M. Sharma, J. CATAL. 160, 80–94 (1996) (solvent washing).

The particular conditions of time, temperature, pressure, and catalyst amount for a specific reaction will need to be determined according to the activity of the reactants. Such adjustments can be readily made by the person skilled in the art. Thus if little or no reaction occurs at a relatively low temperature, or at a relatively low pressure, or using a short reaction time, the conditions can be adjusted by increasing the temperature or reaction time or pressure or by adjusting the catalyst concentration.

PRODUCT: HYDROCARBYL-SUBSTITUTED AMIDE

The present reaction will lead to hydrocarbylation on the nitrogen atom of the nitrile, depending on the specific reaction conditions and the nature of the specific nitrile reactant.

The present invention permits N-hydrocarbyl-substituted amides to be prepared more efficiently without the use of conventional acidic materials such as $AlCl_3$ or sulfuric acid, which cause environmental or handling difficulties, are corrosive, and are not generally reusable. The N-hydrocarbyl-substituted amide products prepared by the present process include such materials as tert-Octyl acrylamide, a hydrophile used in associative thickeners, hair spray resins, and shampoos; and iso-Propyl acrylamide, which displays a lower critical solution temperature in homopolymer form and is useful in controlled drug delivery and thermally-activated gel applications. In a preferred case, the product will be tert-butyl acrylamide, useful in hair-care products, adhesives, water treatment polymers, and oil field polymers.

The N-hydrocarbyl-substituted amide products prepared by the present process also include such materials as 1-chloro-tert-amyl acrylamide, a substance with broad application to cationic resin, paper, oil field, water treatment, and personal care uses; diacetone acrylamide, which is useful in applications ranging from emulsion polymerization to coatings (as methylol derivative) to contact lenses; isopropylidene bisacrylamide, a material used as a cross-linking agent, in non-wovens, and in superabsorbent applications; butenyl acrylamide, a substance with application to graphic arts coatings and photo-curable resins; and acrylamidomethylbutyrate, which has applications in connection with pH-sensitive polymers.

EXAMPLES

Example 1

The partially-exchanged cesium salt of phosphotungstic acid is prepared by the neutralization of phosphotungstic acid, represented by the formula $H_3PW_{12}O_{40}$, with 2.5 equivalents of cesium hydroxide. The product is isolated by evaporation of the excess water. The residual solids are calcined at 320° C. under an air flow for three hours. A 500 ml flask equipped with a magnetic stirrer, a reflux condenser, and an $N_2$ inlet is charged with 5.76 g of $Cs_{2.5}H_{0.5}PW_{12}O_{40}$ catalyst, 13.91 g of tert-butanol, and 99.4 g of acrylonitrile. The reactants are heated to reflux and held there with stirring for 12 hours. Upon cooling to 40° C. the reaction mixture is diluted with methanol, and the mixture is subjected to centrifugation to separate the solids. The liquid phase is stripped under house vacuum at 40° C. to yield 6.14 g of tert-butylacrylamide as a white solid.

Example 2

A 500 ml flask equipped with a mechanical stirrer, an $N_2$ inlet, a reflux condenser, and a dry ice trap is charged with 5.81 g of $Cs_{2.5}H_{0.5}PW_{12}O_{40}$ catalyst prepared according to the procedure of Example 1, 13.8 g of tert-butanol, and 98.4 g of acrylonitrile. The mixture is heated to reflux (approximately 70° C.) and held there with stirring for 12 hours. The reaction mixture is centrifuged to separate out the solid catalyst. The liquid is roto-evaporated then dried to constant weight under vacuum to isolate 6.87 g of tert-butylacrylamide.

Example 3

A 500 ml flask equipped with a mechanical stirrer, an $N_2$ inlet, a reflux condenser, and a dry ice trap is charged with the $Cs_{2.5}H_{0.5}PW_{12}O_{40}$ catalyst isolated and recovered from Example 2, 13.9 g of tert-butanol, and 98.5 g of acrylonitrile. The mixture is heated to reflux and held there with stirring for 12 hours. The reaction mixture is centrifuged to separate out the solid catalyst. The liquid is rotoevaporated then placed under house vacuum overnight to isolate 6.06 g of tert-butylacrylamide.

Example 4

A 500 ml flask equipped with a mechanical stirrer, an $N_2$ inlet, a reflux condenser, and a dry ice trap is charged with the $Cs_{2.5}H_{0.5}PW_{12}O_{40}$ catalyst isolated and recovered from Example 3, 13.6 g of tert-butanol, and 98.7 g of acrylonitrile. The mixture is heated to reflux (approximately 70° C.) and held there with stirring for 12 hours. The reaction mixture is centrifuged to separate out the solid catalyst. The liquid is rotoevaporated then placed under house vacuum overnight to isolate 6.39 g of tert-butylacrylamide.

Example 5

A 500 ml flask equipped with a mechanical stirrer, an $N_2$ inlet, a reflux condenser, and a dry ice trap is charged with the $Cs_{2.5}H_{0.5}PW_{12}O_{40}$ catalyst isolated and recovered from Example 4, 13.8 g of tert-butanol, and 98.7 g of acrylonitrile. The mixture is heated to reflux and held there with stirring for 12 hours. The reaction mixture is centrifuged to separate out the solid catalyst. The liquid is rotoevaporated then placed under house vacuum overnight to isolate 3.51 g of tert-butylacrylamide. The recovered catalyst is washed with methanol and recalcined at 400° C. under an air flow for three hours.

Example 6

A 500 ml flask equipped with a mechanical stirrer, an $N_2$ inlet, a reflux condenser, and a dry ice trap is charged with 4.08 g of the $Cs_{2.5}H_{0.5}PW_{12}O_{40}$ catalyst isolated and recovered from Example 5, 9.6 g of tert-butanol, and 69.2 g of acrylonitrile. The mixture is heated to reflux and held there with stirring for 12 hours. The reaction mixture is centrifuged to separate out the solid catalyst. The liquid is rotoevaporated then placed under house vacuum overnight to isolate 1.92 g of tert-butylacrylamide.

Example 7

A 500 ml flask equipped with a mechanical stirrer, an $N_2$ inlet, a reflux condenser, and a dry ice trap is charged with 5.86 g of $Cs_{2.5}H_{0.5}PW_{12}O_{40}$ prepared according to the procedure of Example 1, 13.8 g of tert-butanol, 98.6 g of acrylonitrile, and 3.35 g of water. The mixture is heated to reflux and held there with stirring for 12 hours. The reaction mixture is centrifuged to separate out the solid catalyst. The liquid is rotoevaporated then placed under house vacuum overnight to isolate 7.98 g of tert-butylacrylamide.

Example 8

A Parr pressure reactor is charged with 2.32 g of $Cs_{2.5}H_{0.5}PW_{12}O_{40}$ catalyst prepared according to the procedure of Example 1, 5.6 g of tert-butanol, and 39.4 g of acrylonitrile. The reactants are stirred and heated at 72° C. for 12 hours. The mixture is then cooled and centrifuged to remove the solid catalyst. The mixture is gravity filtered through paper to ensure separation of the catalyst. The mixture is then placed on a rotary evaporator to isolate 5.73 g of tert-butylacrylamide.

Example 9

A Parr pressure reactor is charged with 2.36 g of $Cs_{2.5}H_{0.5}PW_{12}O_{40}$ catalyst prepared according to the procedure of Example 1, 5.6 g of tert-butanol, and 39.4 g of acrylonitrile. Then, 100 psig $N_2$ is charged to the reactor and reactants are heated to 120° C. After 12 hours, reactants are cooled to 25° C. and centrifuged to remove the solid catalyst. The catalyst is washed with methanol and centrifuged. The supernatants are combined and placed on a rotary evaporator to isolate 8.42 g of tert-butylacrylamide.

Example 10

Phosphotungstic acid represented by the formula $H_3PW_{12}O_{40}$ is coated onto an $SiO_2$ support. A 500 ml flask equipped with a mechanical stirrer, an $N_2$ inlet, a reflux condenser, and a dry ice trap is charged with 5.81 g of the $H_3PW_{12}O_{40}$ catalyst, 13.8 g of tert-butanol, and 98.4 g of acrylonitrile. The reactants are heated to reflux and held there with stirring for 12 hours. The reaction mixture is centrifuged to separate out the solid catalyst. The liquid is rotoevaporated then placed under house vacuum overnight to isolate 10.19 g of tert-butylacrylamide.

Example 11

Phosphotungstic acid represented by the formula $H_3PW_{12}O_{40}$ is coated onto an $SiO_2$ support. A Parr pressure reactor is charged with 2.32 g of the coated $H_3PW_{12}O_{40}$ catalyst, 5.5 g of tert-butanol, and 39.4 g of acrylonitrile. Reactants are heated to 72° C. and held for 12 hours with stirring. After cooling, reactants are centrifuged to remove the $SiO_2$-supported $H_3PW_{12}O_{40}$ catalyst for recycle. Methanol is then added to rinse the Parr reactor. Following centrifugation the reactants are gravity filtered through paper and placed on a rotary evaporator to isolate 4.13 g of tert-butylacrylamide.

Example 12

A Parr pressure reactor is charged with 2.32 g of the $SiO_2$-supported $H_3PW_{12}O_{40}$ catalyst isolated and recovered from Example 11, 5.5 g of tert-butanol, and 39.4 g of acrylonitrile. Reactants are heated to 72° C. and held for 12 hours with stirring. After cooling, reactants are centrifuged to remove the $SiO_2$-supported $H_3PW_{12}O_{40}$ catalyst for recycle. Methanol is added to rinse the Parr reactor. Following centrifugation the reactants are gravity filtered through paper and placed on a rotary evaporator to isolate 0.50 g of tert-butylacrylamide. The recovered $SiO_2$-supported $H_3PW_{12}O_{40}$ is prepared for recycle by twice washing with DMF [N,N-dimethylformamide] and drying in dessicator under house vacuum.

Example 13

A Parr pressure reactor is charged with 1.44 g of the $SiO_2$-supported $H_3PW_{12}O_{40}$ catalyst isolated and recovered from Example 12, 5.5 g of tert-butanol, and 39.1 g of acrylonitrile. Reactants are heated to 72° C. and held for 12 hours with stirring. After cooling, reactants are centrifuged to remove the $SiO_2$-supported $H_3PW_{12}O_{40}$ catalyst. Following centrifugation the reactants are gravity filtered through paper and placed on a rotary evaporator to isolate 0.18 g of tert-butylacrylamide.

Example 14

A 500 ml flask equipped with a mechanical stirrer, an $N_2$ inlet, a reflux condenser, and a dry ice trap is charged with 5.81 g of $H_3PMo_{12}O_{40}$ coated onto an $SiO_2$ support, 13.8 g of tert-butanol, and 98.5 g of acrylonitrile inhibited with 35–45 ppm hydroquinone monomethyl ether. The mixture is heated to reflux and held there with stirring for 12 hours. The reaction mixture is centrifuged to separate out the solid catalyst. The liquid is rotoevaporated then placed under house vacuum overnight to isolate 7.43 g of tert-butylacrylamide.

Example 15

A Parr pressure reactor is charged with 2.32 g of $Cs_{2.5}H_{0.5}PW_{12}O_{40}$ catalyst prepared according to the procedure of Example 1, 38.7 g of acrylonitrile, 5.61 g of tert-butanol, and 0.18 g of MEHQ and sealed with an air head space. The contents are heated at 72° C. with stirring for 8 hours, cooled overnight, then heated at 72° C. with stirring for 4 more hours, for a total reaction time of 12 hours. Solids are removed by centrifugation. The liquid phase is reduced to constant weight on a rotary evaporator to isolate 3.89 g of tert-butylacrylamide. The $Cs_{2.5}H_{0.5}PW_{12}O_{40}$ catalyst is isolated and recovered for recycle.

Example 16

A Parr pressure reactor is charged with about 2.32 g of the $Cs_{2.5}H_{0.5}PW_{12}O_{40}$ catalyst isolated and recovered from Example 15, 38.7 g of acrylonitrile, 5.61 g of tert-butanol, and 0.18 g of MEHQ. The reactor is sealed with an air head space. The contents are heated to 72° C. and held for 12 hours with maximum stirring. Solids are removed by centrifugation. The liquid phase is reduced to constant weight on a rotary evaporator to isolate 1.43 g of tert-butylacrylamide. The $Cs_{2.5}H_{0.5}PW_{12}O_{40}$ catalyst is isolated and recovered for recycle.

Example 17

A Parr pressure reactor is charged with about 2.32 g of the $Cs_{2.5}H_{0.5}PW_{12}O_{40}$ catalyst isolated and recovered from Example 16, 38.7 g of acrylonitrile, 5.61 g of tert-butanol, and 0.18 g MEHQ. The reactor is sealed with air in the head space. The contents are heated to 72° C. and held for 12 hours with maximum stirring. Then, solids are removed by centrifugation. Finally, the liquid phase is reduced to constant weight on a rotary evaporator to isolate 0.73 g of tert-butylacrylamide.

Example 18

A cesium phosphotungstate catalyst is prepared according to the procedure of Example 1. A Parr pressure reactor is charged with 2.05 g of $Cs_{2.5}H_{0.5}PW_{12}O_{40}$, 32.24 g of acrylonitrile plus 30 ppm MEHQ, 13.54 g of 2,4,4 trimethyl-1-pentene, 3.27 g of distilled $H_2O$, and 0.025 g of MEHQ. The reactor is sealed with air in the head space. The contents are heated to 120° C. for 12 hours, developing a pressure of 50 psig. Upon cooling the contents are diluted with toluene and centrifuged to separate the solids. The liquid organic phase is reduced to constant weight on a rotary evaporator with heating up to 45° C. to isolate 2.07 g of 2,4,4-trimethylpentylacrylamide.

Example 19

A supported phosphomolybdic catalyst is prepared by coating a molybdenum heteropolyacid represented by the formula $H_3PMo_{12}O_{40}$ onto a silica support represented by the formula $SiO_2$ in the ratio of one part phosphomolybdic acid to four parts silica. A Parr pressure reactor containing a stainless steel basket in turn containing 2.32 g of the $H_3PMo_{12}O_{40}/SiO_2$ catalyst in 1/16" extrudate form is charged with 38.7 g of acrylonitrile with 35 ppm MEHQ, and 5.61 g of tert-butanol. The reactor is sealed with air in the head space. The contents are heated to 72° C. for 12 hours with maximum stirring. The reactor is cooled and the liquid is removed. The liquid is reduced to constant weight on a rotary evaporator to isolate 2.1 g of tert-butylacrylamide. The $SiO_2$-supported $H_3PMo_{12}O_{40}$ catalyst is isolated and recovered for recycle.

Example 20

A Parr pressure reactor containing a stainless steel basket in turn containing about 2.32 g of $H_3PMo_{12}O_{40}/SiO_2$ catalyst in 1/16" extrudate form recovered for recycle from Example 19, is charged with 38.7 g of acrylonitrile and 5.61 g of tert-butanol. The reactor is sealed with air in the head space. The contents are heated at 72° C. for 12 hours with maximum stirring. Upon cooling to room temperature the liquid is removed, filtered, and reduced to constant weight on a rotary evaporator to isolate 0.2 g of tert-butylacrylamide.

Example 21

A cesium phosphotungstate catalyst is prepared according to the procedure of Example 1. A Parr pressure reactor is charged with 2.32 g of $Cs_{2.5}H_{0.5}PW_{12}O_{40}$, 52.40 g of acrylonitrile, and 5.94 g of isopropanol. The reactor is sealed with air in the head space. The contents are heated to 120° C. and held at that temperature for 12 hours with maximum stirring. The $Cs_{2.5}H_{0.5}PW_{12}O_{40}$ catalyst is then separated from the liquid phase by filtration. The liquid is reduced to constant weight on a rotary evaporator at a temperature of 40° C. and under house vacuum to isolate 0.85 g of isopropylacrylamide.

Example 22

A cesium phosphotungstate catalyst is prepared according to the procedure of Example 1. A heavy-walled glass reaction tube equipped with a magnetic stirrer is charged with 1.13 g of the $Cs_{2.5}H_{0.5}PW_{12}O_{40}$, 18.8 g of butyronitrile, and 2.02 g of tert-butanol. The tube is sealed with a Teflon® cap. The contents are heated in an oil bath to 72° C. for 12 hours with stirring. The $Cs_{2.5}H_{0.5}PW_{12}O_{40}$ catalyst is then separated from the liquid phase by centrifugation and set aside for recycle. The liquid is reduced to constant weight on a rotary evaporator to isolate 0.85 g of tert-butylbutyramide.

Example 23

A heavy-walled glass reaction tube equipped with a magnetic stirrer is charged with about 1.13 g of the $Cs_{2.5}H_{0.5}PW_{12}O_{40}$ catalyst recovered for recycle from Example 22, 18.30 g of butyronitrile, and 2.02 g of tert-butanol. The tube is sealed with a ®Teflon cap. The contents are heated in an oil bath to 72° C. for 12 hours with stirring. The $Cs_{2.5}H_{0.5}PW_{12}O_{40}$ catalyst is then separated from the liquid phase by centrifugation and recovered for recycle. The liquid is reduced to constant weight on a rotary evaporator to isolate 0.53 g of tert-butyl butyramide.

Example 24

A heavy-walled glass reaction tube equipped with a magnetic stirrer is charged with about 1.13 g of the $Cs_{2.5}H_{0.5}PW_{12}O_{40}$, recovered for recycle from Example 23, 18.02 g of butyronitrile, and 2.01 g of tert-butanol. The tube is sealed with a Teflon® cap. The contents are heated in an oil bath to 72° C. for 12 hours with stirring. The $Cs_{2.5}H_{0.5}PW_{12}O_{40}$ catalyst is then separated from the liquid phase by centrifugation and recovered for recycle. The liquid is reduced to constant weight on a rotary evaporator to isolate 0.42 g of tert-butylbutyramide.

Example 25

A heavy-walled glass reaction tube equipped with a magnetic stirrer is charged with about 1.13 g of the $Cs_{2.5}H_{0.5}PW_{12}O_{40}$ catalyst recovered for recycle from Example 24, 18.21 g of butyronitrile, and 1.96 g of tert-butanol. The tube is sealed with a Teflon cap. The contents are heated in an oil bath to 72° C. for 12 hours with stirring. The $Cs_{2.5}H_{0.5}PW_{12}O_{40}$ is then separated from the liquid phase by centrifugation and recovered for recycle. The liquid is reduced to constant weight on a rotary evaporator to isolate 0.37 g of tert-butylbutyramide.

Example 26

The $Cs_{2.5}H_{0.5}PW_{12}O_{40}$ recovered for recycle in Example 25 is dried and heat-treated at up to 450° C. under an air flow for 3 hours and then held for 1 hour. A heavy-walled glass reaction tube equipped with a magnetic stirrer is charged with about 1.13 g of the heat-treated $Cs_{2.5}H_{0.5}PW_{12}O_{40}$ recovered for recycle from Example 25, 9.75 g of butyronitrile, and 1.05 g of tert-butanol. The tube is sealed with a Teflon® cap. The contents are heated in an oil bath to 72° C. for 12 hours with stirring. The liquid is reduced to constant weight on a rotary evaporator to isolate 0.39 g of tert-butylbutyramide.

Example 27

A cesium phosphotungstate catalyst is prepared according to the procedure of Example 1. A heavy-walled glass reaction tube equipped with a magnetic stirrer is charged with 1.48 g of $Cs_{2.5}H_{0.5}PW_{12}O_{40}$, 24.73 g of acrylonitrile, 3.46 g of tert-butanol, and 4.20 g of $H_2O$. The contents are heated in an oil bath to 72° C. for 12 hours with constant stirring. The organic phase is reduced to constant weight on a rotary evaporator and dried in an oven under vacuum to isolate 0.15 g of tert-butylacrylamide.

Example 28

An ammonium phosphotungstate catalyst is prepared by reacting 2.5 equivalents of ammonium chloride represented by the formula $NH_4Cl$ with 1 equivalent of phosphotungstic acid represented by the formula $H_3PW_{12}O_{40}$ to form ammonium phosphotungstate represented by the formula $(NH_4)_{2.5}H_{0.5}PW_{12}O_{40}$. A heavy-walled glass reaction tube equipped with a magnetic stirrer is charged with 1.21 g of $(NH_4)_{2.5}H_{0.5}PW_{12}O_{40}$, 24.88 g of acrylonitrile, and 3.48 g of tert-butanol. The tube is sealed and the contents are heated by an oil bath to 72° C. for 12 hours with constant stirring. The solids are removed by centrifugation and the $(NH_4)_{2.5}H_{0.5}PW_{12}O_{40}$ is recovered for recycle. The liquid phase is reduced to constant weight on a rotary evaporator to isolate 1.83 g of tert-butylacrylamide.

Example 29

Approximately 1.21 g of the $(NH_4)_{2.5}H_{0.5}PW_{12}O_{40}$ catalyst isolated and recovered for recycle in Example 28, 25.20 g of acrylonitrile, and 3.53 g of tert-butanol are charged to a glass reaction tube. The tube is sealed and the contents are heated in an oil bath to 72° C. for 12 hours with constant stirring. The solids are removed by centrifugation and the $(NH_4)_{2.5}H_{0.5}PW_{12}O_{40}$ catalyst is again recovered for recycle. The liquid phase is reduced to constant weight on a rotary evaporator to isolate 1.01 g of tert-butylacrylamide.

Example 30

A cesium phosphotungstate catalyst is prepared according to the procedure of Example 1. A 500 ml round bottomed flask equipped with a reflux condensor, a cold finger with dry ice, a mechanical stirrer, and a heating mantle, is charged with 6.50 g of the $Cs_{2.5}H_{0.5}PW_{12}O_{40}$, 151.60 g of EMKROX AF-20®, a propoxylated $C_{14-16}$ alcohol, and 91.8 g of acrylonitrile. The contents are heated at 75° C. for 16 hours with constant stirring. The solids are then removed by centrifugation. The liquid is stripped at 110° C. under house vacuum to yield 129.7 g of product.

Example 31

The partially-exchanged aluminum salt of phosphotungstic acid is prepared by the neutralization of phosphotungstic acid, represented by the formula $H_3PW_{12}O_{40}$, with 0.83 equivalents of aluminum nitrate, represented by the formula $Al(NO_3)_3$. A glass reaction tube equipped with a magnetic stirrer is charged with 1.18 g of the $Al_{0.83}H_{0.5}PW_{12}O_{40}$, 27.73 g of acrylonitrile, and 3.40 g of tert-butanol. The contents are heated at 72° C. for 12 hours with stirring. The reaction tube is cooled to room temperature and centrifuged to remove solids. The liquid phase is reduced to constant weight under vacuum to yield 3.75 g of tert-butylacrylamide.

Example 32

A supported phosphotungstic catalyst is prepared by coating a tungsten heteropolyacid represented by the formula $H_3PW_{12}O_{40}$, onto a silica support represented by the formula $SiO_2$ in the ratio of one part phosphotungstic acid to four parts silica. A solution comprising 20.73 g of acrylonitrile and 3.51 g of tert-butanol is pumped at a rate of 0.200 ml/min from an Isco® syringe pump at room temperature through a transfer line heated to 70° C. into the bottom of a continuous reactor comprising a reflux condenser packed with 11.93 g (28 cc displacement) of the silica supported catalyst in the form of 1/16" extrudate, quartz chips, and glass wool packed above and below the catalyst zone. The water jacket of the continuous reactor is heated by pumping 75° C. water from a heated bath using a peristaltic pump. Over a residence time of 140 minutes, 24.25 g of product solution is collected with a dry ice trap from the continuous reactor then rotary evaporated to constant weight to yield 0.70 g of tert-butylacrylamide. The silica-supported phosphotungstic catalyst is recovered for recycle.

Example 33

A solution comprising 34.20 g of acrylonitrile and 5.79 g of tert-butanol is pumped at a rate of 0.200 ml/min from an Isco® syringe pump at room temperature through a transfer line heated to 70° C. into the bottom of a continuous reactor comprising a reflux condenser packed with 11.93 g (28 cc displacement) of the silica-supported catalyst in the form of 1/16" extrudate recovered for recycle from Example 32, quartz chips, and glass wool packed above and below the catalyst zone. The water jacket of the continuous reactor is heated by pumping 75° C. water from a heated bath using a peristaltic pump. Over a residence time of 140 minutes, 40.02 g of product solution is collected with a dry ice trap from the continuous reactor then rotary evaporated to constant weight to yield 2.19 g of tert-butylacrylamide.

Example 34

A supported aluminum phosphotungstic catalyst is prepared by coating a partially exchanged aluminum salt of phosphotungstic acid prepared according to the method of Example 31, represented by the formula $Al_{0.83}H_{0.5}PW_{12}O_{40}$, onto a silica support represented by the formula $SiO_2$ in the ratio of one part aluminum phosphotungstic acid to four parts silica. Into a 100 ml Parr pressure reactor are charged 3.01 g of the supported catalyst in the form of 1/16" extrudate within a stainless steel mesh basket, 49.21 g of acrylonitrile, and 8.34 g of tert-butanol. The Parr reactor is sealed with air in the headspace and heated to 72° C. with maximum stirring for 12 hours. The reactants are cooled to room temperature and the liquid is removed. The liquid is reduced to constant weight on a rotary evaporator to yield 3.81 g of tert-butylacrylamide. The supported aluminum phosphotungstic acid catalyst is recovered for recycle.

Example 35

Into a 100 ml Parr pressure reactor are charged 3.01 g of the supported catalyst in the form of 1/16" extrudate within a stainless steel mesh basket recovered for recycle from Example 34, 47.40 g of acrylonitrile, and 8.04 g of tert-butanol. The Parr reactor is sealed with air in the headspace and heated to 72° C. with maximum stirring for 12 hours. The reactants are cooled to room temperature and the liquid is removed. The liquid is reduced to constant weight on a rotary evaporator to yield 1.17 g of tert-butylacrylamide.

Example 36

The partially-exchanged aluminum salt of phosphomolybdic acid is prepared by the neutralization of phosphomolybdic acid, represented by the formula $H_3PMo_{12}O_{40}$, with 0.83 equivalents of aluminum nitrate, represented by the formula $Al(NO_3)_3$. A glass reaction tube equipped with a magnetic stirrer is charged with 1.16 g of the $Al_{0.83}H_{0.5}PMo_{12}O_{40}$, 23.26 g of acrylonitrile, and 3.94 g of tert-butanol. The contents are heated at 72° C. for 12 hours with stirring. The reaction tube is cooled to room temperature and centrifuged to remove solids. The liquid phase is reduced to constant weight on a rotary evaporator to yield 2.99 g of tert-butylacrylamide.

Example 37

The partially-exchanged cesium salt of phosphomolybdic acid is prepared by the neutralization of phosphomolybdic acid, represented by the formula $H_3PMo_{12}O_{40}$, with 1.25 equivalents of cesium carbonate, represented by the formula $Cs_2CO_3$. A glass reaction tube equipped with a magnetic stirrer is charged with 1.17 g of the $Cs_{2.5}H_{0.5}PMo_{12}O_{40}$, 23.55 g of acrylonitrile, and 3.99 g of tert-butanol. The contents are heated at 72° C. for 12 hours with stirring. The reaction tube is cooled to room temperature and centrifuged to remove solids. The liquid phase is reduced to constant weight on a rotary evaporator to yield 1.50 g of tert-butylacrylamide.

Example 38

To a five-gallon autoclave are charged 317 g of the partially-exchanged salt of phosphotungstic acid represented by the formula $Cs_{2.5}H_{0.5}PW_{12}O_{40}$ prepared according to the method of Example 1, 740 g of tert-butanol, and 5,300 g of acrylonitrile. The autoclave is charged to 100 psig with $N_2$ and sealed. Autoclave is heated with stirring to 120° C. for 12 hours during which time pressure rises to 100-150 psig. Reactor is cooled to room temperature, depressurized, and opened. Reaction mixture is centrifuged to remove catalyst. Clear reaction mixture is removed and catalyst residue is saved for recycle. The reaction mixture is stripped at reduced pressure and resulting residue is dried at reduced pressure. Distillate is saved for recycle.

Example 39

To a large glass water-jacketed condenser with a glass wool plug on either end is charged 200 g of a silica-supported phosphomolybdic catalyst represented by the formula $H_3PMo_{12}O_{40}$ prepared according to the method of Example 19. Water at 75° C. from a constant temperature bath is fed into the jacket of the condenser and recirculated through the constant temperature bath. A mixture comprising 740 g of tert-butanol and 5,300 g of acrylonitrile is fed into the bottom of the condenser at a rate of 1.4 ml/min (liquid) for a residence time of 140 minutes. The reactor is allowed to equilibrate for three hours before product is collected. The effluent is collected from the top of the reactor in a 1000 ml collection flask which is periodically drained and the resulting product is isolated by stripping at reduced pressure. The distillate from the stripping is collected and placed in a separate container for use in a recycle stream. The resulting solid residue is dried at reduced pressure.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. As used herein, the expression "consisting essentially of" permits the inclusion of substances which do not materially affect the basic and novel characteristics of the composition under consideration.

What is claimed is:

1. A process for the preparation of a hydrocarbyl-substituted amide, comprising contacting:
   (a) a nitrile with
   (b) a hydrocarbylating agent, in the presence of
   (c) a catalyst comprising a heteropolyacid or salt thereof
under conditions leading to the formation of the hydrocarbyl-substituted amide.

2. The process of claim 1 wherein the nitrile is unsaturated.
3. The process of claim 1 wherein the nitrile is saturated.
4. The process of claim 2 wherein the nitrile is acrylonitrile.
5. The process of claim 3 wherein the nitrile is butyronitrile.
6. The process of claim 1 wherein a condition leading to the formation of the hydrocarbyl-substituted amide comprises contacting at least one mole of water per mole of component (b) with components (a), (b), and (c).
7. The process of claim 1 wherein the hydrocarbylating agent comprises an olefin.
8. The process of claim 7 wherein the olefin is a branched-chain olefin.
9. The process of claim 7 wherein the olefin contains an average of about 2 to about 200 carbon atoms.
10. The process of claim 8 wherein the branched-chain olefin is 2-methyl-1-propene.
11. The process of claim g wherein the branched-chain olefin is trimethylpentene.
12. The process of claim 1 wherein the hydrocarbylating agent is an alcohol.
13. The process of claim 12 wherein the alcohol is a secondary alcohol.
14. The process of claim 12 wherein the alcohol is a tertiary alcohol.
15. The process of claim 13 wherein the secondary alcohol is 2-propanol.
16. The process of claim 14 wherein the tertiary alcohol is 2-methyl-2-propanol.
17. The process of claim 1 wherein the hydrocarbylating agent is substituted with at least one non-hydrocarbon group.
18. The process of claim 17 wherein the hydrocarbylating agent is substituted with at least one alkoxy group.
19. The process of claim 18 wherein the hydrocarbylating agent is drawn from a mixture of propoxylated $C_{14}$–$C_{16}$ alcohols.
20. The process of claim 18 wherein the hydrocarbylating agent is an alkoxylated alcohol.
21. The process of claim 1 wherein the catalyst is present in an amount of about 0.1 percent to about 50 percent by weight of the reaction mixture.
22. The process of claim 20 wherein the catalyst is present in an amount of about 1 percent to about 15 percent by weight of the reaction mixture.
23. The process of claim 1 wherein the catalyst is a phosphotungstate, a phosphomolybdate, a phosphotungstic acid, or a phosphomolybdic acid.
24. The process of claim 23 wherein the catalyst is a phosphotungstic acid represented by the formula $H_3PW_{12}O_{40}$.
25. The process of claim 23 wherein the catalyst is a phosphotungstate.
26. The process of claim 25 wherein the phosphotungstate is a partially-exchanged cesium salt.
27. The process of claim 26 wherein the partially-exchanged cesium salt contains an average of about 2.5 cesium ions and about 0.5 hydrogen ions per structural unit.
28. The process of claim 27 wherein the partially-exchanged cesium salt is represented by the formula $Cs_{2.5}H_{0.5}PW_{12}O_{40}$.
29. The process of claim 25 wherein the phosphotungstate is a partially-exchanged aluminum salt.
30. The process of claim 29 wherein the partially-exchanged aluminum salt contains an average of about 0.83 aluminum ions and about 0.5 hydrogen ions per structural unit.
31. The process of claim 30 wherein the partially-exchanged aluminum salt is represented by the formula $Al_{0.83}H_{0.5}PW_{12}O_{40}$.
32. The process of claim 25 wherein the phosphotungstate is a partially-exchanged ammonium salt.
33. The process of claim 32 wherein the partially-exchanged ammonium salt contains an average of about 2.5 ammonium ions and about 0.5 hydrogen ions per structural unit.
34. The process of claim 33 wherein the partially-exchanged ammonium salt is represented by the formula $(NH_4)_{2.5}H_{0.5}PW_{12}O_{40}$.
35. The process of claim 23 wherein the catalyst is a phosphomolybdic acid represented by the formula $H_3PMo_{12}O_{40}$.
36. The process of claim 23 wherein the catalyst is a phosphomolybdate.
37. The process of claim 36 wherein the phosphomolybdate is a partially exchanged cesium salt.
38. The process of claim 37 wherein the partially-exchanged cesium salt contains an average of about 2.5 cesium ions and about 0.5 hydrogen ions per structural unit.
39. The process of claim 38 wherein the partially-exchanged cesium salt is represented by the formula $Cs_{2.5}H_{0.5}PMo_{12}O_{40}$.
40. The process of claim 36 wherein the phosphomolybdate is a partially exchanged aluminum salt.
41. The process of claim 40 wherein the partially-exchanged aluminum salt contains an average of about 0.83 aluminum ions and about 0.5 hydrogen ions per structural unit.
42. The process of claim 41 wherein the partially-exchanged aluminum salt is represented by the formula $Al_{0.83}H_{0.5}PMo_{12}O_{40}$.
43. The process of claim 1 wherein the catalyst contains zero or more than zero waters of hydration per structural unit.
44. The process of claim 43 wherein the catalyst contains an average of up to about 40 waters of hydration per structural unit.
45. The process of claim 43 wherein the catalyst contains an average of up to about 5 waters of hydration per structural unit.
46. The process of claim 1 wherein the catalyst has been subjected to heat treatment prior to use.
47. The process of claim 46 wherein the heat treatment is conducted at an average temperature of at least about 100° C.

48. The process of claim 46 wherein the heat treatment is conducted at an average temperature of at least about 150° C.

49. The process of claim 46 wherein the heat treatment is conducted at an average temperature of at least about 300° C.

50. The process of claim 46 wherein the heat treatment is conducted at an average temperature in the range from about 400° C. to about 500° C.

51. The process of claim 1 wherein the process is conducted at an average temperature in the range from about −10° C. to about 400° C.

52. The process of claim 51 wherein the process is conducted at an average temperature in the range from about 25° C. to about 250° C.

53. The process of claim 51 wherein the process is conducted at an average temperature in the range from about 60° C. to about 100° C.

54. The process of claim 1 wherein the process is conducted at an average pressure in the range from about 1 atmosphere to about 20 atmospheres.

55. The process of claim 54 wherein the process is conducted at an average pressure in the range from about 2 atmospheres to about 15 atmospheres.

56. The process of claim 1 wherein the catalyst is provided on a solid support.

57. The process of claim 56 wherein the solid support is provided in substantially cylindrical form.

58. The process of claim 56 wherein the support is alumina, an aluminophosphate, carbon, clay, magnesia, silica, silica/alumina, titania, a zeolite, or zirconia.

59. The process of claim 56 wherein the support is silica.

60. The process of claim 59 wherein the ratio of catalyst to silica is from about 0.5:99.5 to about 50:50.

61. The process of claim 59 wherein the ratio of catalyst to silica is from about 3:97 to about 40:60.

62. The process of claim 1 wherein the process is a continuous process.

63. The process of claim 62 wherein the process is conducted in a continuous stirred tank reactor.

64. The process of claim 62 wherein the process is a continuous plug flow process.

65. The process of claim 62 wherein the process is conducted in a tubular reactor.

66. The process of claim 62 wherein the process has an average liquid hourly space velocity in the range from about 0.01 to about 100.

67. The process of claim 66 wherein the process has an average liquid hourly space velocity in the range from about 1 to about 10.

68. The process of claim 23 wherein the catalyst is a partially exchanged metal salt.

* * * * *